US00PP21938P2

(12) United States Plant Patent
Bradford

(10) Patent No.: US PP21,938 P2
(45) Date of Patent: May 31, 2011

(54) INTERSPECIFIC TREE NAMED 'BLACKRED XI'

(50) Latin Name: ***Prunus* sp.**
Varietal Denomination: Blackred XI

(76) Inventor: Lowell Glen Bradford, Le Grand, CA (US)

( * ) Notice: Subject to any disclaimer, the term of this patent is extended or adjusted under 35 U.S.C. 154(b) by 0 days.

(21) Appl. No.: 12/655,116

(22) Filed: Dec. 24, 2009

(51) Int. Cl.
*A01H 5/00* (2006.01)

(52) U.S. Cl. ..... Plt./180

(58) Field of Classification Search ..... Plt./180
See application file for complete search history.

(56) References Cited

U.S. PATENT DOCUMENTS

PP14,220 P2 10/2003 Bradford
PP19,576 P2 12/2008 Bradford

*Primary Examiner* — Susan B McCormick Ewoldt

(57) ABSTRACT

The present invention relates to an interspecific tree and more particularly to a new and distinct variety broadly characterized by a medium size, vigorous, hardy, and very productive tree. Being self-unfruitful, the present variety requires cross pollination from an apricot, plum, or interspecific variety that blooms during the mid to late season, such as 'Blackred V' (U.S. Plant Pat. No. 19,576). The present variety's abundance of blossoms and pollen entices strong bee activity to facilitate pollination. The fruit matures under the ecological conditions described early September, with first picking on Sep. 7, 2009. The fruit is medium to large in size, almost entirely black in skin color, clingstone in type, nearly globose in shape, and mostly red in flesh color.

1 Drawing Sheet

Botanical classification: *Prunus* sp.
Varietal denomination: 'BLACKRED XI'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits. The present invention relates to a new and distinct variety of interspecific tree which has been denominated varietally as 'Blackred XI'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2003 one such house containing an unpatented purple plum, code named '42P1156', was crossed by me in this manner. To pollinate this purple plum, I selected bouquets from several sources of apricot and interspecific plum-apricot hybrid trees without keeping specific written details. Upon reaching maturity the fruit from this plum tree was harvested and the seeds were removed, cracked, stratified and germinated as a group with the label "H12". They were grown as seedlings on their own root in my greenhouse and upon reaching dormancy transplanted to a cultivated area of my experimental orchard located near Le Grand, Calif. in Merced County (San Joaquin Valley). During the summer of 2006 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is similar to its seed parent, '42P1156', by being self-unfruitful and by producing fruit that is purple to black in skin color, firm in texture, and globose in shape, but is distinguished therefrom by producing fruit that is pink to red in flesh color instead of yellow, that is much sweeter in flavor, and that matures about thirty days later.

The present variety is similar to 'September Yummy' plum (U.S. Plant Pat. No. 14,220) by being self-unfruitful and by producing fruit that ripens in the late season, that is firm in texture, and that is very good in flavor, but is distinguished therefrom by producing fruit that is mostly black in skin color instead of red, that is more heavily red in flesh color, that is clingstone instead of semi-freestone, and that matures about thirty days earlier. It is to be noted that the patent for 'September Yummy' plum describes a first pick date of Sep. 10, 2002. Since the filing of that patent, it has been established that the average commercial first pick date is closer to October 10th.

The present variety is most similar to 'Blackred XII' interspecific tree (U.S. Plant Pat. No. 20,892) by being self-unfruitful and by producing fruit that is clingstone in type, that is mostly globose in shape, that matures in the late season, that is very good in flavor, that is mostly black in skin color, and that is mostly red in flesh color, but is distinguished therefrom by producing fruit that is somewhat larger in size and that matures about two weeks earlier.

SUMMARY OF VARIETY

The present interspecific variety is characterized by a medium size, vigorous, hardy, and very productive tree. Being self-unfruitful, the present variety requires cross pollination from an apricot, plum, or interspecific variety that blooms during the mid to late season, such as 'Blackred V' (U.S. Plant Pat. No. 19,576). The present variety's abundance of blossoms and pollen entices strong bee activity to facilitate pollination. The fruit matures under the ecological conditions described early September, with first picking on Sep. 7, 2009. The fruit is medium to large in size, almost entirely black in skin color, clingstone in type, nearly globose in shape, and mostly red in flesh color.

DRAWING

The accompanying photograph consists of four whole fruits positioned to display the characteristics of the skin color and form, two half fruits divided to reveal the flesh and stone, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of full shipping ripe on Sep. 14, 2009, on the original tree during its sixth growing season. The flower and bud descriptions were developed during the previous blooming season. All major color code designations are by reference to the Inter-Society Color Council, National Bureau of Standards. Common color names are also used occasionally.

PARENTAGE

Seed parent: '42P1156' plum (unpatented).
Pollen parent: Unknown.

TREE

Size: Medium, reaching a height of 14' [4.27 m.] and a spread of 7' [2.13 m.] after six growing seasons utilizing typical pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Parallel V form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Heavy production, thinning usually necessary.

Fertility: Self-unfruitful, requiring cross pollination by a suitable mid to late seasonal blooming apricot, interspecific, or plum, such as 'Blackred V' interspecific tree (U.S. Plant Pat. No. 19,576).

Bearing: Regular bearer, with no crop failures observed.

Trunk:

*Size.*—Medium, reaching a maximum diameter of 4" [102 mm.] after the sixth growing season.

*Texture.*—Shaggy.

*Bark color.*—A Light brownish gray [63. 1.brGy] and Dark grayish brown [62. d.gyBr] variegation with Deep yellowish brown [75. deep yBr] crevices present.

*Lenticels.*—Approximate Number Per Square Inch: 6. Color: Strong yellowish brown [74. s.yBr]. Average Size: 7/16" [11.1 mm.]. Shape: Elongated, eye-shaped.

Branches:

*Size.*—Diameter of main scaffold is 2¼" [57.2 mm.] measured 12" above the crotch, diameter of secondary limb is 1¼" [31.8 mm.] measured 12" above the first fork.

*Texture.*—Smooth on first and second year wood, increasing roughness with age.

*Color.*—1st Year Wood: Deep yellowish brown [75. deep yBr]. 2nd Year Wood: Deep yellowish brown [75. deep yBr]. Older wood: A Light brownish gray [63. 1.brGr] and Moderate yellowish brown [77. m.yBr] variegation.

*Lenticels.*—Number Per Square Inch: About 80 on second year wood. Color: Light yellowish brown [76. 1.yBr]. Average size: 1/16" [1.6 mm.]. Shape: Elongated, eye-shaped.

Leaves:

*Size. Medium. Average length:* 3⅝" [92 mm.]. Average width: 1⅜" [35 mm.].

*Arrangement.*—Alternate.

*Thickness.*—Medium.

*Form.*—Elliptical.

*Apex.*—Acuminate.

*Base.*—Acute with an average angle base angle of 60 degrees.

*Surface.*—Smooth.

*Color.*—Dorsal surface: Moderate olive green [125. m.OlG]. Ventral surface: Moderate yellow green [120. m.YG].

*Margin.*—Finely serrate.

*Venation.*—Pinnately net veined.

*Petiole.*—Average length: ⅜" [9.5 mm.]. Average thickness: 1/16" [1.6 mm.]. Color: Pale yellow green [121. p.YG] with Deep red [13. deep R] topsides on some.

*Stipules.*—Number: Usually 2 per leaf, up to 6 per growing tip. Average length: ¼" [6.4 mm.]. Color: Grayish olive green [127. gy.OlG] becoming Moderate reddish brown [43. m.rBr] with age.

*Glands.*—Number: Mostly 2 to 4 per leaf. Position: Oppositely positioned at the intersection of the petiole and the leaf blade. Size: Medium. Form: Globose. Color: Light yellow green [119. 1.YG] acquiring a Grayish olive green [127. gy.OlG] center with age.

*Leaf buds.*—Pointed, medium.

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Tip color.*—White [263. White].

Flowers: Perfect, complete, perigynous, usually a single pistil, about thirty stamens, five sepals and petal locations alternately positioned.

*Average flower diameter.*—1 1/16" [27.0 mm.].

*Number of petals.*—Five, no double blossoms observed.

*Petal shape.*—Oval to circular.
*Petal margin.*—Entire, smooth to slightly wavy.
*Average petal diameter.*—½" [12.7 mm.].
*Average petal length.*—⅝" [15.9 mm.].
*Petal apex.*—Rounded.
*Petal base.*—Obtuse.
*Petal color.*—White [263. White] on both sides.
*Anther color.*—Strong orange yellow [68. s.OY] over a Light orange yellow [70. 1.OY] background.
*Stigma color.*—Pale yellow green [121. p.YG].
*Sepal color.*—Brilliant yellow green [116. brill.YG] on the outer surface with Grayish pink [8. gy.Pk] areas toward the edges.
*Sepal length.*—11/64" [4.4 mm.].
*Sepal width.*—9/64" [3.6 mm.].
*Sepal apex.*—Rounded to elliptical to match the width and length.
*Sepal margin.*—Fairly smooth, with slight serration toward the apex.
*Average pistil length.*—11/16" [17.5 mm.].
*Average stamen length.*—½" [12.7 mm.].
*Fragrance.*—Moderate.
*Pollen production.*—Strong, bee enticing.
*Blooming period.*—Medium to late, four days before 'Santa Rosa' plum (unpatented).
*Onset of bloom.*—One percent on Feb. 22, 2009.
*Date of full bloom.*—Mar. 2, 2009.
*Duration of bloom.*—One to two weeks, dependent on ambient temperature.
*Bloom density.*—Very heavy.
*Number per cluster.*—2 to 9, average 4.

FRUIT

Maturity when described: Full shipping ripe, Sep. 14, 2009.
Date of first picking: Sep. 7, 2009.
Date of last picking: Sep. 21, 2009.
Size: Uniform, Large.
*Average diameter axially.*—2½" [63.5 mm.].
*Average diameter across cheek plane.*—2¾" [69.9 mm.].
*Average diameter across suture plane.*—2⅝" [66.7 mm.].
*Typical Weight.*—6.1 ounces [173 grams].
Form: Uniform, symmetrical, globose to slightly oblate.
*Longitudinal section form.*—Globose to slightly oblate.
*Transverse section through diameter.*—Round.
Suture: An inconspicuous line located in a shallow groove extending from the base to the pistil point.
Ventral surface: Rounded strongly, lipped on both sides.
Lips: Slightly unequal.
Cavity: Flaring, circular, suture showing on one side.
*Depth.*—⅜" [9.5 mm.].
*Breadth.*—11/16" [17.5 mm.].
Base: Rounded to somewhat truncate.
Apex: Rounded to slightly truncate.
Pistil point: An inconspicuous Strong yellowish Brown [74. s.yBr] dot located at the end of the suture.
Stem: Medium.
*Average length.*—7/16" [11.1 mm.].
*Average width.*—1/16" [1.6 mm.].
Skin:
*Thickness.*—Medium.
*Surface.*—Smooth.
*Tenacity.*—Tenacious to the flesh.
*Astringency.*—Nonastringent.
*Tendency to crack.*—None observed in dry season.
*Color.*—Blackish purple [230. bk.P] with very slight Pale yellow green [121. p.YG] freckling throughout.
*Bloom.*—Abundant.
Flesh:
*Color.*—Strong yellowish pink [26. s.yPk] toward the stone with an abundance of Very red [11. v.R] streaking and bleeding, especially toward the skin.
*Surface of pit cavity.*—Covered with Moderate yellowish pink [29. m.yPk] broken fibers when twisted away from stone.
*Amygdalin.*—Moderate.
*Juice.*—Abundant, rich.
*Texture.*—Firm, tough, meaty.
*Fibers.*—Abundant.
*Ripens.*—Slightly earliest toward the apex.
*Flavor.*—A tasty balance of acid and sugar, typically 23 brix.
*Aroma.*—Moderate.
*Eating quality.*—Excellent.

STONE

Type: Clingstone.
Form: Oval.
Hilum: Narrow, oblong.
Base: Rounded to somewhat obtuse.
Apex: Acuminate.
Sides: Equal.
Surface: Rough, some irregular furrows and ridges mostly near the base.
External color of stone: Grayish greenish yellow [105. gy.gY] when first removed.
Pit wall color when cracked: Moderate greenish yellow [102. m.gY].
Cavity surface color: Light olive [106. 1.Ol].
Average pit wall thickness: ⅛" [3.2 mm.].
Average width: 11/16" [17.5 mm.].
Average length: 15/16" [23.8 mm.].
Average breadth: 7/16" [11.1 mm.].
Tendency to split: None.
Kernel:
*Form.*—Oval.
*Skin color.*—Brownish orange [54. brO].
*Pellicle color.*—Dark grayish yellowish brown [81. d.gy.yBr].
*Vein color.*—Deep yellowish brown [75. deep yBr].
*Taste.*—Slightly bitter.
*Viable.*—Yes.
*Average width.*—7/16" [11.1 mm.].
*Average length.*—9/16" [14.3 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to 'Blackred XII' interspecific tree (U.S. Plant Pat. No. 20,892) by being self-unfruitful and by producing fruit that is clingstone in type, that is mostly globose in shape, that matures in the late season, that is very good in flavor, that is mostly black in skin color, and that is mostly red in flesh color, but is distinguished therefrom by producing fruit that is somewhat larger in size and that matures about two weeks earlier.

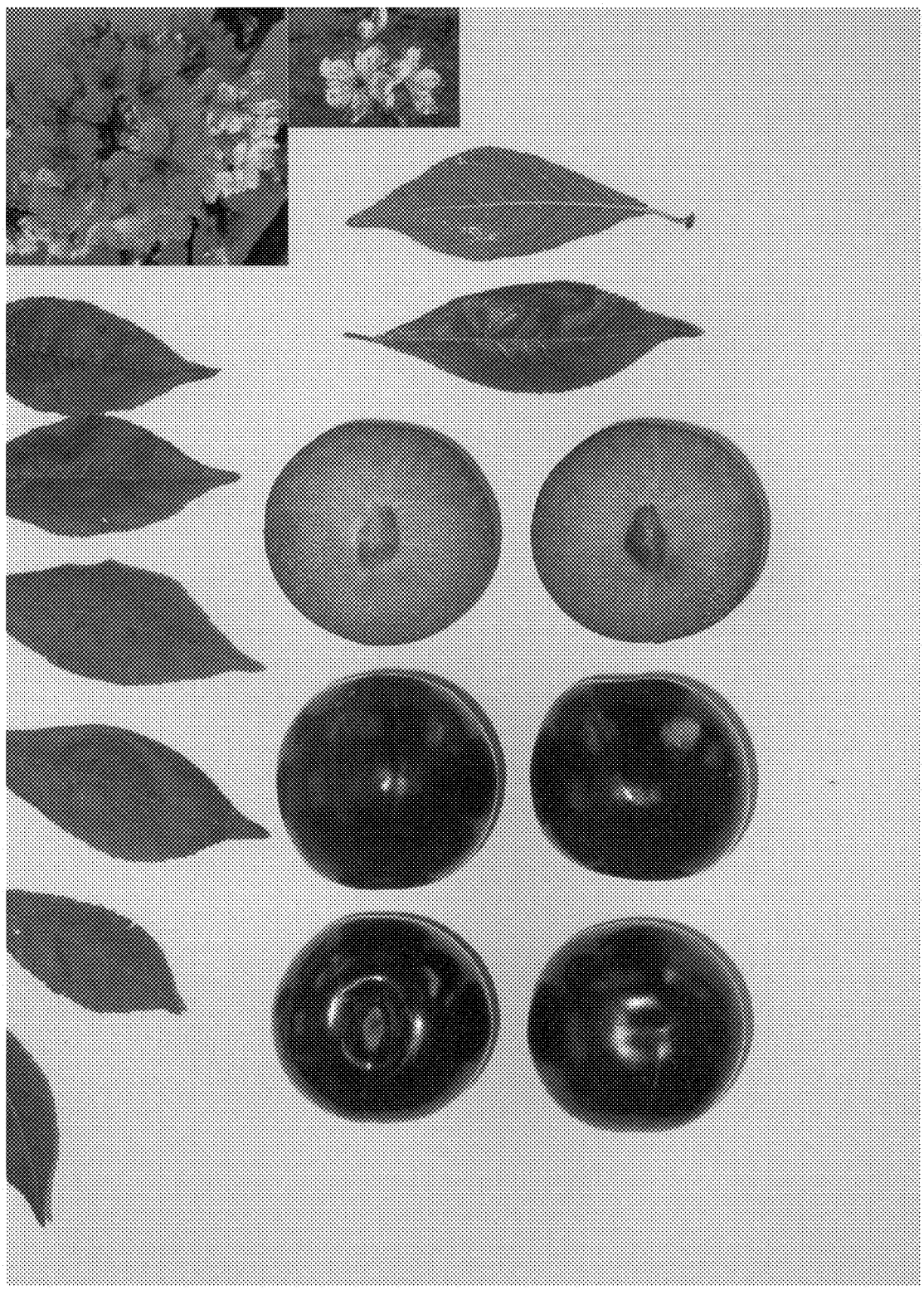

* * * * *